United States Patent [19]

Clausen et al.

[11] Patent Number: 4,921,504
[45] Date of Patent: May 1, 1990

[54] 4-(N-ETHYL-N-2-HYDROXYETHYL)-AMINO-1-(2 HYDROXYETHYL)-AMINO-2-NITROBENZENE AND COMPOSITIONS FOR DYEING HAIR CONTAINING THE SAME

[75] Inventors: Thomas Clausen, Alsbach; Eugen Konrad, Darmstadt, both of Fed. Rep. of Germany

[73] Assignee: Wella Aktiengesellschaft, Darmstadt, Fed. Rep. of Germany

[21] Appl. No.: 244,534

[22] Filed: Sep. 12, 1988

Related U.S. Application Data

[63] Continuation of Ser. No. 24,898, Mar. 11, 1987, abandoned, which is a continuation of Ser. No. 801,619, Nov. 25, 1985, abandoned.

[30] Foreign Application Priority Data

Nov. 24, 1984 [DE] Fed. Rep. of Germany ....... 3442861

[51] Int. Cl.$^5$ .................. C09B 51/00; C07C 91/40
[52] U.S. Cl. .......................................... 8/415; 564/441
[58] Field of Search ............................ 564/441; 8/415

[56] References Cited

U.S. PATENT DOCUMENTS 3,274,249  9/1966  Brunner et al. ................... 8/415 X

FOREIGN PATENT DOCUMENTS 900490   5/1972  Canada .
1017750  7/1959  Fed. Rep. of Germany .
1299002  7/1969  Fed. Rep. of Germany .
1569807  1/1970  Fed. Rep. of Germany .
1569808  7/1970  Fed. Rep. of Germany .

OTHER PUBLICATIONS

Colour Index, third Edition, vol. 4, published by The Society of Dyers and Colourists.
J. C. Johnson, *Hair Dyes*, Noyes Data Corp., Park Ridge (U.S.A.) (1973).

Primary Examiner—Charles F. Warren
Assistant Examiner—Carolyn S. Elmore
Attorney, Agent, or Firm—Michael J. Striker

[57] ABSTRACT

The compound 4-(N-ethyl-N-2'-hydroxyethyl)-amino-1-(2''-hydroxyethyl)-amino-2-nitrobenzene, having the formula:

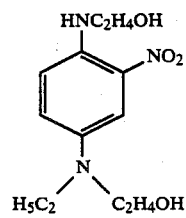

is provided for use as a blue coloring nitro dye in a hair dyeing composition that may be directly applied to hair without the use of oxidation agents.

6 Claims, No Drawings

4-(N-ETHYL-N-2-HYDROXYETHYL)-AMINO-1-(2 HYDROXYETHYL)-AMINO-2-NITROBENZENE AND COMPOSITIONS FOR DYEING HAIR CONTAINING THE SAME

This application is a continuation of application Ser. No. 024,898, filed Mar. 11, 1987, now abandoned, which is turn a continuation of application Ser. No. 801,619 filed Nov. 25, 1985, now abandoned.

The present invention relates to the new compound 4-(N-ethyl-N-2'-hydroxyethyl)-amino-1-(2''-hydroxyethyl)-amino-2-nitrobenzene having the structural formula that follows, and its application as a component in compositions for dyeing of hair.

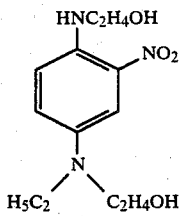

Nitro dyes have a wide application nowadays in hair dyeing compositions. By combining a plurality of different nitro dyes, hair may be dyed in natural and fashionable tones without the use of oxidation agents. For example, natural hair colors may be made by combining a blue with an orange dye or by combining a blue with a pure yellow and a red nitro dye.

As part of the foregoing technique of carefully combining different colored dyes, there is a recognized need for a blue nitro dye which must be generally recognized as safe in toxicological and dermatological respects and must allow for the creation of colorations in the desired intensity which, among other things, assumes a good water solubility. Additionally, a good light, acid and friction genuiness is required for the obtained hair dyes.

Currently, the method for obtaining blue nitro dyes generally involves producing trialkalized 2-nitro-p-phenylenediamine derivatives of the general formula II:

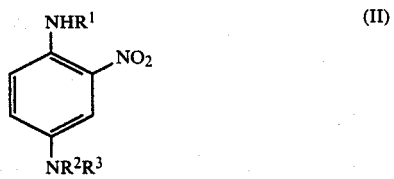

Numerous tests were already made to make dyes which meet the aforesaid requirements. As isomer of compound I, the 1-ethyl amino compound III,

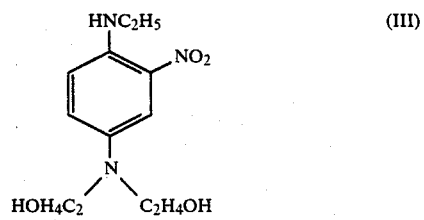

(compare, for example, DE-OS 1 569 808) is currently used in hair dyes. The poor solubility of compound III of below 0.15% in water without also having to dissolve intermediaries prevents use of the compound in quantities in emulsion systems which are required for obtaining a high dye intensity.

In contrast thereto, the high solubility of the trihydroxyethyl compound IV, mentioned in DE-PS 1 017 750,

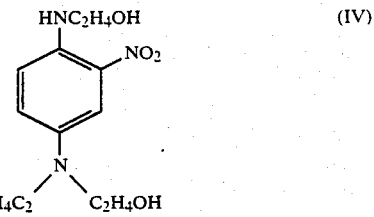

results in a good applicability in high concentrations, but the dye because of its good water solubility is very quickly rinsed out during the washing of the hair, so that the necessary genuiness is not satisfactory.

The aforementioned problems are not as pronounced when using the 1-methyl amino compound V

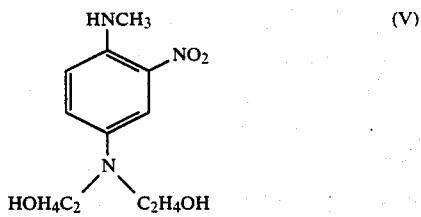

in accordance with DE-PS 1 299 002. However, the acquisition of dark shapes can be made more difficult by the low solubility of this compound being only about 0.5%. Moreover, doubts have recently been raised regarding the safe use of this compound, i.e., the possibly unacceptable level of toxicity of compound V.

Furthermore, an isomer of compound V, compound VI (DE-PS 15 69 807 and CA-PS 900 490), which is recommended over compound V, is also not completely satisfactory: On the one hand, it is criticized as having a mutagenic effect in the Ames test, on the other hand, in comparison with formula I, it shows a reddish cromatic aberration which renders difficult the shading of natural tones.

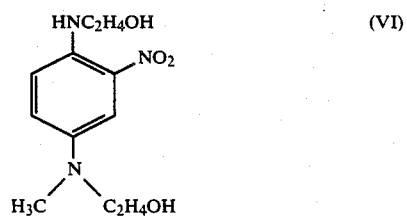

In view of the foregoing, it was most surprising to find the blue nitro dye (compound I), being an isomer of compound III and a homologue of compound VI, has sufficiently different characteristics which cannot be derived from known compounds III, IV, V or VI. The dye (I) in accordance with the present invention has a solubility of about 1.0% in water which facilitates the acquisition of dark shades considerably, particularly, in comparison with compound III. Moreover, compound I does not crystallize when exceeding solubility due to the low melting point of 62° C. of the inventive compound. Rather, an oil is formed from which the dye can later be supplied during the dyeing process. The alternative of redissolving formed crystals would take too much time and, as a result, such crystals would not, again, be available during the dyeing process.

In contrast to the good solubility of compound IV, the inventive compound in accordance with the present invention does not possess the undesirable effect of easily washing out.

The described characteristics are also responsible for the extraordinary storage stability of dyes using compound I, particularly in the dye compositions to be discussed hereinafter. Moreover, the light genuiness of the nitro dyes containing compound I is also very good.

It should be recognized that toxicological considerations play a decisive role in the selection of a dye; this factor is in addition to the necessary technical requirements of such dyes. It has been surprisingly discovered that the inventive compound (I) is safe when compared with compounds II through VI:
Compound I is not mutagenic in four test systems:
 1. Ames test
 2. yeast cell-mutagenity test
 3. mouse-lymphoma-assay
 4. human-lymphocyte-test
Compound I has a high $LD_{50}$ in the range of 2 g/kg
Compound I shows a good skin compatibility The manufacture of the dye in accordance with the present invention can be carried out in a number of ways, e.g., by ethylizing 1,4-bis-(2'-hydroxyethylamino)-2-nitrobenzene or by ethylizing 2-nitro-p-phenylene-diamine and subsequent hydroxy ethylizing on N-1 and N-4. The latter method is described in an example hereinafter.

Therefore, the present invention provides compositions for dyeing hair with a dye content and customary cosmetic additives that contain the inventive compound of formula I. The compositions in accordance with the invention relate, in particular, to dyes which can be applied without the addition of an oxidation agent. Such hair dyeing compositions may contain other dyes which can be directly applied to the hair, in addition to the inventive blue nitro dye compound. Among the currently known dyes which may be combined with the blue nitro dye utilizing the inventive compound are, by way of example, those dyes included within the following classes:

Aromatic nitro dyes (e.g., 1,2-diamino-4-nitrobenzene, 1-amino-4-(2',3'-dihydroxypropyl)-amino-5-chloro-2-nitrobenzene, 1amino-2-(2'-hydroxyethyl)-amino-5-nitrobenzene, 1-amino-2-nitro-4-bis-(2'-hydroxyethyl)-aminobenzene, 4-(2'-ureidoethyl)-amino-nitrobenzene, picramic acid, 2-(2'-hydroxyethyl)-amino-4,6-dinitrophenol, 4-(2',3'-dihydroxypropyl)-amino-3-nitrotoluene, 4-(2'-hydroxyethyl)-amino-3-nitrochlorobenzene, azo dyes (e.g., Acid Brown 4, C.I. 14,805), anthraquinone dyes (e.g., Disperse Blue 23, C.I. 61,545 and Disperse Violet 4, C.I. 61,105), triphenyl methane dyes (e.g., Basic Violet 1, C.I. 61,100), wherein the dyes of these classes may have an acid, nonionogenic or basic character depending on the presence of certain substituents. Additional dyes which can be directly applied to the hair are, for example, described in the book by J. C. Johnson, *Hair Dyes*, Noyes Data Corp., Park Ridge (U.S.A.) (1973).

Natural tones, fashionable blond and brown tones and shining fashionable tones having an excellent stability may be made with hair dyes which contain mixtures of the aforesaid dyes.

The form of preparation of the hair dye compositions described, on the basis of dyes which can be directly applied to the hair, may be by solution, in particular, e.g., an aqueous or aqueous-alcoholic solution. Preferred forms of preparation are creams, gels or emulsions. In addition, the hair dye compositions described may also be sprayed via a mixture with a propulsion gas or by means of a pump.

Customary additives in solutions, creams, emulsions or gels are, for example, solvents, like water, low molecular aliphatic alcohols, e.g., ethanol, propanol, isopropanol, glycerins or glycols, such as ethylene glycol and propylene glycol or glycol ethers. Furthermore, wetting agents or emulsifiers from the classes of anionic, cationic, amphoteric or nonionogenic surface active substances, e.g., fatty alcohol sulfates, fatty alcohol ether sulfates, alkyl sulfonates, alkylbenzol sulfates, alkyltrimethyl ammonium salts, alkylbetaine, oxethylized fatty alcohols, oxethylized nonylphenols, fatty acid alcohol amides, oxethylized fatty acid esters are possible additives. Additional additives include thickeners, e.g., higher fatty alcohols, bentonite, starch, polyacrylic acid, cellulose derivatives, for example, carboxyl methyl cellulose, alginates, Vaseline ®, paraffin oil and fatty acids as well as caring products, e.g., lanolin derivatives, cholesterin, pantothenic acid and betaine, furthermore, perfume oils and complex formers. The above-mentioned constituents are used in amounts which are customary for such purposes, for example, the wetting agents and emulsifiers are used in concentrations of about 0.5–30%, by weight, while thickeners may be contained in amounts from about 0.1–25%, by weight, in the preparations.

The inventive compound of formula I should be contained in hair dye compositions in a concentration from about 0.01 to 2.0% by weight preferably from 0.01 to 1.0% by weight. The total content of dyes should be in the range of about 0.01 to 3.0%, by weight, of the composition.

The pH-value of these dye compositions is in the range of 3–10.5, in particular, pH 7.5–9.5, wherein the adjustment of the desired pH-value is performed primarily with ammonia, however, organic amines, for example, monoethanol amine or triethanol amine can also be used.

The hair dyeing compositions utilizing the inventive compound are applied to the hair in the customary manner and should remain in contact with the hair for between 5 and 30 minutes. Subsequently, rinsing is performed with water and, if necessary, also with a weak organic acid followed by drying. As the weak organic acid, e.g., acetic acid, citric acid and wine vinegar may be used.

The aforesaid hair dyeing compositions may naturally contain cosmetic polymerisates, whereby a strengthening, or fastening, of the hair is obtained simultaneously with the dyeing of the hair. Such compositions are generally called tone fixers or color fixers.

Of the polymerisates which are known in cosmetics for this purpose, worthy of mention, by way of example, are polyvinyl pyrrolidone, polyvinyl acetate, polyvinyl alcohol or polyacryl compositions, e.g., acrylic acid or methacrylic acid polymerisates. Basic polymerisates of esters from acrylic acid or methacrylic acid and amino alcohols or the salts thereof or quaternization products, polyacryl nitrile, polyvinyl lactam as well as copolymerisates from such compounds as e.g., polyvinyl pyrrolidone-vinyl acetate, are further examples.

Additionally, natural polymerisates, e.g., chitosan (deacetylized chitin) or chitosan derivatives may also be used for the above-mentioned purpose.

The polymerisates are contained in the dyeing compositions by the customary amounts of about 1–4% by weight. The pH-values of these compositions are in the range of about 6.0–9.5.

The application of these hair dyes with additional strengthening or fastening of the hair is performed in the known and customary manner by moistening the hair with the fastener, fastening (i.e., setting) the hair into a hairdo and, subsequently, drying the hair.

Naturally, the aforesaid described hair dye compositions may contain additional customary cosmetic additives, if need be, e.g., caring substances, wetting agents, thickeners, softeners, preservation substances, anti-dandruff active substances and perfume oils.

The invention will now be more fully described by the following examples. It should, however, be noted that such examples are given by way of illustration and not of limitation.

HAIR DYE EXAMPLES

Example 1

The liquid hair dye composition of:

| | |
|---|---|
| 1.00 g | dye compound in accordance with formula I |
| 0.50 g | hydroxyethyl cellulose |
| 5.00 g | lauryl alcohol-diglycol ether sulfate-sodium salt, 28% aqueous solution |
| 15.00 g | isopropyl alcohol |
| 0.03 g | ammonia, 25% |
| 78.47 g | water |
| 100.00 g | | is applied to white human hair and reacts thereon for 10 minutes. The hair is dyed in a dark blue, after rinsing with water and drying.

Example 2

Dye fixer

| | |
|---|---|
| 0.02 g | dye compound in accordance with formula I |
| 2.00 g | polyvinyl pyrrolidone |
| 0.10 g | glycerin |
| 40.00 g | isopropyl alcohol |
| 57.88 g | water |
| 100.00 g | |

White human hair is set with the fastening dye solution and dried. The hair assumes a pleasant silver-blue glimmer.

Example 3

Hair dye composition in gel form

| | |
|---|---|
| 1.0 g | dye in accordance with formula I |
| 0.3 g | 1-amino-4-(2',3'-dihydroxypropyl)-amino-5-chloro-2-nitrobenzene |
| 0.1 g | 4-(2'-ureidoethyl)amino-nitrobezene |
| 17.5 g | oleic acid |
| 7.5 g | isopropanol |
| 9.0 g | ammonia, 25% |
| 64.6 g | water |

| | |
|---|---|
| 100.00 g | |

The aforesaid hair dyeing composition is applied to gray human hair and reacts thereon for 30 minutes. Thereafter, it is rinsed with water and dried. The hair has a dark blond coloration with mahogany colored reflexes.

Example 4

Hair dyeing composition in cream form

| | |
|---|---|
| 0.03 g | dye compound in accordance with formula I, used as a hydrochloride |
| 0.05 g | 1-amino-2-(2'-hydroxyethyl)-amino-5-nitrobenzene |
| 0.02 g | 1-amino-2-nitro-4-bis-(2'hydroxyethyl)-aminobenzene |
| 0.025 g | Disperse Blue 23, C.I. 61,545 |
| 7.5 g | cetyl alcohol |
| 1.75 g | lauryl alcohol-diglycol ether sulfate-sodium salt, 28% aqueous solution |
| 0.1 g | p-hydroxy benzoic acid methyl ester |
| 0.2 g | ammonia, 25% |
| 90.055 g | water |
| 100.00 g | |

50 g of the aforementioned hair dye composition are applied to white human hair which is rinsed with water after a reaction time of 20 minutes. Subsequently, the hair is dried. It is dyed in a natural brown color tone.

MANUFACTURING EXAMPLE

Stage 1

1-amino-4-benzosulfonamido-2-nitrobenzene 153 g (1.0 mole) 1,4-diamino-2-nitrobenzene are suspended in 525 ml of 24% potassium hydroxide solution (2.2 moles). 193 g (1.1 moles) benzene sulfonic acid chloride are added dropwise while stirring. The solution is heated for a short time, whereupon a yellow precipitate appears. The deposit is poured onto water and is filtered off from the precipitate by afterwashing. The residue is then dried. As a result, one obtains the sulfonamide in almost a quantitative yield. The melting range after recrystallization from dioxane is 162°–163° C.

Stage 2

1-amino-4-N-ethyl-benzolsulfonamido-2-nitrobenzene 58.6 g (0.2 moles) of the sulfonamide from Stage 1 are dissolved in 300 ml ethanol and reacted with a solution of 17 g (0.3 moles) potassium hydroxide in a small amount of water and with 31 g (0.2 moles) ethyl iodide. This mixture is heated to 70° C. and then after 5 hours, 5.6 g (0.1 moles) potassium hydroxide in a small amount of water and 15.2 g (0.1 moles) ethyl iodide are added. After another 3 hours, the mixture is cooled off, whereupon the ethyl composition crystallizes in the form of yellow flakes. The result one obtains is 25 g (39% of the theoretical yield) of the ethyl compound having a melting point of 152° C.

Stage 3

1-amino-4-ethylamino-2-nitrobenzene 25.0 g (87 mmoles) of the sulfonamide from Stage 2 are heated in 50 ml of 50% (volume-percent) sulfuric acid for 30 minutes to 130° C. After this time, no turbity occurs during the dilution of the sample with water so that the sulfonamide is completely separated. One then pours the sample onto water and neutralizes with ammonia. During cooling, an oily separating base gels first. The result one obtains is 13.0 g (93% of the theoretical yield) of a 4-ethylamino compound having a melting point of 53° C.

Stage 4

4-(N-ethyl-N-2'-hydroxyethyl)-amino-1-(2'''-hydroxyethyl)-amino-2-nitrobenzene 13 g (72 mmoles) 1-amino-4-ethylamino-2-nitrobenzene from Stage 3 are dissolved in 23 g (286 mmoles) 2-chloroethanol. This mixture is then heated to 140° C. and a solution of 11.5 g (286 mmoles) sodium hydroxide is slowly added dropwise to 110 ml water while stirring. After 5 hours, the same amount of 2-chloroethanol is added and again a corresponding amount of sodium lye is added dropwise. After the alkylization is substantially completed (after 10 hours), the mixture is cooled and extracted with acetic acid ethyl ester. The combined acetic ester phases are dried over sodium sulfate and the solvent is evaporated in a vacuum. The oily residue is dissolved in 30 ml isopropanol and is reacted with 5 ml concentrated hydrochloric acid. The hydrochloride precipitates in the form of yellow crystals. The crystals are filtered off and the residue is dried. As a result, one obtains 6 g (27% of the theoretical yield) of the hydrochloride of compound I, the inventive compound, which is in an impurified form with a small amount of 1-amino-4-(N-ethyl-N-2'-hydroxyethyl)-amino-2-nitrobenzene.

The pure dye compound (I) can be recovered from the oily residue of the acetic ester extraction by means of chromatography on silica gel with acetic ester as the operating substance. The pure base melts at 62° C.

| | Elementary analysis: | |
| --- | --- | --- |
| | calculated | found |
| C | 53.52 | 53.72 |
| H | 7.11 | 7.17 |
| N | 15.60 | 15.54 |

While only several embodiments and examples of the present invention have been shown and described, it is obvious that many changes and modifications may be made thereunto, without departing from the spirit and scope of the invention.

What is claimed is:

1. A composition for dyeing human hair, in the form of an aqueous or aqueous alcoholic solution, creme, gel or emulsion, which comprises a cosmetically effective amount of 4-(N-ethyl-N-2'-hydroxyethyl)-amino-1-(2''-hydroxyethyl)-amino-2-nitrobenzene and a cosmetically acceptable non-toxic carrier or diluent.

2. The composition according to claim 1, wherein said composition contains 0.01–2.0%, by weight, 4-(N-ethyl-N-2'-hydroxyethyl)-amino-1-(2''-hydroxyethyl)-amino-2-nitrobenzene.

3. The composition according to claim 1, further comprising a cosmetic preparation in an aqueous-alcoholic solution for the purpose of hair fastening.

4. The composition according to claim 1, wherein said composition has a pH of between 6.0–9.5.

5. The composition according to claim 1, further comprising known dyes that are capable of being directly applied to hair selected from the group consisting of 1-amino-4-(2',3'-dihydroxypropyl)-amino-5-chloro-2-nitrobenzene, 4-(2'-ureidoethyl)amino-nitrobenzene, 1-amino-2-nitro-4-bis-(2'-hydroxyethyl)-aminobenzene, 1-amino-2-(2'-hydroxyethyl)-amino-5-nitrobenzene, picramic acid, 2-(2'-hydroxyethyl)-amino-4,6-dinitrophenyl, 4-(2',3'-dihydroxypropyl)-amino-3-nitrotoluene, 4-(2'-hydroxyethyl)-amino-3-nitrochlorobenzene, Acid Brown 4 (C.I. 14,805), Disperse Violet 4 (C.I. 61,105), Disperse Blue 23 (C.I. 61,545), Basic Violet 1 (C.I. 61,100) and a combination thereof.

6. 4-(N-ethyl-N-2'-hydroxyethyl)-amino-1-(2''-hydroxethyl)-amino-2-nitrobenzene.

* * * * *